United States Patent [19]
Nelson

[11] Patent Number: 5,982,847
[45] Date of Patent: Nov. 9, 1999

[54] COMPACT X-RAY FLUORESCENCE SPECTROMETER FOR REAL-TIME WEAR METAL ANALYSIS OF LUBRUCATING OILS

[75] Inventor: Irina Nelson, Murray, Utah

[73] Assignee: Utah State University, Logan, Utah

[21] Appl. No.: 08/958,415

[22] Filed: Oct. 27, 1997

Related U.S. Application Data

[60] Provisional application No. 06/029,490, Oct. 28, 1996.

[51] Int. Cl.$^6$ .................................................. G01N 23/223
[52] U.S. Cl. ................................................. 378/47; 378/45
[58] Field of Search ................................. 378/44, 45, 46, 378/47, 48, 49, 84, 85; 250/505.1

[56] References Cited

U.S. PATENT DOCUMENTS

| | | | |
|---|---|---|---|
| 3,751,661 | 8/1973 | Packer et al. | 378/47 |
| 5,497,008 | 3/1996 | Kumakhov | 250/505.1 |
| 5,598,451 | 1/1997 | Ohno et al. | 378/44 |

*Primary Examiner*—David P. Porta
*Attorney, Agent, or Firm*—Workman, Nydegger & Seeley

[57] ABSTRACT

A compact X-ray fluorescence spectrometer system dedicated to in-line, real-time analysis of wear metal particles in a lubricant used in a lubricating system that comprises a sample chamber, an X-ray source assembly, and an X-ray detector assembly. The sample chamber is substantially composed of a non-metallic material and has a cylindrical shape. The sample chamber is adapted for in-line connection to the lubrication system of the machine such that the sample chamber provides a passageway through which the lubricant flows. The sample chamber has an X-ray transparent window formed therein that allows the passage of X-rays so that the presence of wear metal particles can be detected in the lubricant. A high intensity, relatively small spot incident X-ray source assembly is configured to provide a source of X-rays directed toward the sample chamber such that said X-rays pass through the window in the sample chamber and contact the lubricant flowing therethrough. The X-ray source assembly may comprise either an electron-beam excited X-ray tube associated with a collimating/focusing assembly or, alternatively, an X-ray laser source. The X-ray detector assembly is configured to detect the X-rays emitted from the lubricant flowing through the sample chamber. The X-ray detector assembly generates a signal reflecting the X-rays emitted by the lubricant and comprises a collimating/focusing assembly capable of wide angle collection of the X-rays emitted from the lubricant flowing though the sample chamber and a low-noise X-ray detector. The system also includes a computer system and associated software for processing the signal in order to determine the presence and amount of wear metal particles in said lubricant.

43 Claims, 10 Drawing Sheets

5,982,847

COMPACT X-RAY FLUORESCENCE SPECTROMETER FOR REAL-TIME WEAR METAL ANALYSIS OF LUBRUCATING OILS

RELATED APPLICATIONS

The benefit of the earlier filing date of a Provisional Patent Application Ser. No. 60/029,490, filed Oct. 28, 1996, is claimed for this application under 35 U.S.C. § 119(e).

BACKGROUND OF THE INVENTION

1. The Field of the Invention

The present invention relates to spectrometers, and particularly to X-ray fluorescence spectrometers for wear metal analysis of lubricating oils.

2. Relevant Technology

The presence of wear metal particles in lubricating oils, even in micron or sub-micron size is recognized as one of the main causes of catastrophic failure of aircraft engines, gear boxes, and other lubricated machinery. The American Society of Mechanical Engineers ("ASME") has established standard ASME industrial assessment charts such as the one depicted in FIG. 1, indicating industrial tolerance limits for various chemical elements. Some types of equipment require even more stringent standards. For example, advanced military aircraft engines, have a limit for the maximum iron content for safe engine operation that is typically set at about four (4) parts per million ("ppm"). This is a much lower limit than the range of 20 ppm to 50 ppm established by one ASME industrial assessment chart for general industrial facilities as indicated by FIG. 1.

Depending on the type of equipment, the risk of failure, and the stringentness of the tolerance limits, periodic inspections are performed to verify that the wear metal particles are not exceeding established tolerances. For example, after a number of in-flight occurrences resulting in the loss of crew and hardware, the risk of engine failure was deemed to be so serious by the military that an oil analysis for F16 fighter airplanes is currently performed after every flight.

At present, wear metal analysis is routinely performed in dedicated analytical laboratories on solid residual particles collected from used oils by filtration after selected periods of operation, such as 10, 50, 100, and 500 hours of operation. The most common analysis methods are: atomic emission spectroscopy; inductively coupled plasma spectroscopy; atomic absorption spectroscopy; and X-ray fluorescence spectroscopy. Atomic emission spectroscopy is a destructive method in which a sample material is excited by arc sparks that are produced in a sample chamber to cause a subsequent characteristic emission. Inductively coupled plasma spectroscopy is also a destructive method. In inductively coupled plasma spectroscopy a sample is excited by burning it in a high temperature furnace to produce a plasma. Atomic absorption spectroscopy is a destructive inspection method in which the molecular disassociation or ionization of the sample is related to characteristic reductions in the intensity of an incident light beam passing through the sample. The X-ray fluorescence spectroscopy is a non-destructive inspection method where a sample is excited by exposure to an X-ray beam and as the energy dissipates releases a characteristic emission.

In certain field cases, periodic batch sampling and emission or absorption analyses are sufficiently reliable to detect over ninety percent (90%) of potential failures. This level of performance is, however, considered insufficient or unacceptable if, even in singular cases, loss of human life and of unique, expensive hardware is involved. Moreover, emission and absorption spectroscopies are sensitive only to solid particles of a size in the 1 micron to 10 micron range. Thus, these methods cannot be used for advanced engine systems in which special filters prevent the passage of particles larger than 0.3 microns.

A particular deficiency of the inductively coupled plasma spectroscopy is that the short, high temperature burning of the batch specimens usually lasting only nanoseconds to microseconds may not be capable of vaporizing large wear metal particles. These limitations of absorption and emission spectroscopies suggest that X-ray fluorescence spectroscopy should rather be adopted as a preferred analytical method.

X-ray fluorescence spectroscopy has no particle size limitation, and is fast, reliable, and non-destructive. In current applications, however, X-ray fluorescence spectroscopy is still performed in the batch mode. A batch mode is when the sample materials, in this case the solid particles, are collected periodically from used oils by a filtration process. Therefore, in spite of the advantages of the X-ray fluorescence spectroscopy method, the formation and release of wear metal particles into the system may still escape immediate detection with possible catastrophic results. On the other hand, oil analyses performed with virtually arbitrary periodicity, without any reliable indication of actual significant wear, are expensive in terms of materials, equipment, labor, and time.

X-ray fluorescence spectroscopy is one of the analytical methods often used for elemental identification and quantitative evaluation of components in multi-element sample materials. A schematic illustration of the basic two-stage process involved in X-ray fluorescence spectroscopy is shown in FIGS. 2 and 3. In the first stage or X-ray absorption stage, energy, such as an X-ray, is delivered to the sample material from an external X-ray source as depicted in FIG. 2. The energy absorption or energy increase results in the sample becoming excited at the atomic level as shown in FIG. 3. In the second stage or the X-ray emission stage, after a time interval equal to the life time of the characteristic excited state, the sample spontaneously decays and emits the excess energy in the form of X-rays with energies uniquely related to the electronic structure of the sample species as illustrated in FIG. 3.

The emission spectrum is plotted as X-ray intensity versus energy. The line features of the emitted X-ray spectrum are characteristic for the chemical composition of the sample material and thus can be interpreted as fingerprints in a virtually unequivocal elemental identification. Line intensities are used in quantitative analyses with appropriate calibration. The bremsstrahlung radiation background, always present in the recorded spectrum, can be subtracted by a computer used for data processing.

It would be advantageous to substantially improve the efficiency of early risk detection by incorporating a miniature analytical instrument within the machinery assembly itself to conduct a continuous, real-time oil analysis and detection of metal particles of any size. It would be advantageous to be able to have an X-ray fluorescence spectroscopy that did not have to be run in a batch mode. It would further be advantageous to be able to have immediate detection of the formation and release of wear metal particles.

SUMMARY AND OBJECTS OF THE INVENTION

It is an object of the present invention to provide X-ray fluorescence spectroscopy systems that are capable of performing immediate detection of the formation and release of wear metal particles within a lubrication system of a machine.

Another objective of the present invention is to provide rugged, miniaturized X-ray fluorescence spectroscopy systems.

Another object of the present invention is to provide X-ray fluorescence spectroscopy systems in which data collection is fast enough that it can be used for real time analysis.

Yet another object of the present invention is to provide X-ray fluorescence spectroscopy systems that can be used to inspect wear metal particles of substantially any size.

A further object of the present invention is to provide X-ray fluorescence spectroscopy systems in which the recorded spectrum has the capability of providing elemental identification of wear metal particles.

A further object of the present invention is to provide X-ray fluorescence spectroscopy systems that are reliable and accurate.

Additional objects and advantages of the invention will be set forth in the description which follows, and in part will be obvious from the description, or may be learned by the practice of the invention. The objects and advantages of the invention may be realized and obtained by means of the instruments and combinations particularly pointed out in the appended claims.

To achieve the foregoing objects, and in accordance with the invention as embodied and broadly described herein a miniaturized and in-line X-ray fluorescence spectroscopy system is provided to perform a real-time analysis of a lubricant in a lubrication system of a machine. The X-ray fluorescence spectroscopy system excites a lubricant sample using X-rays and upon the energy from the sample decaying a characteristic elemental emission is emitted by the lubricant that provides a measurement and identification of the presence and concentration of wear metal particles in the lubricant. Anticipated users of the X-ray fluorescence spectroscopy system include the military and civilian aircraft industry, spacecraft industry, automotive industry, and other industries employing a variety of lubricated moving parts and mechanisms.

The X-ray fluorescence spectroscopy system is dedicated to an in-line, real-time analysis of wear metal particles in the lubricant of a lubricating system, and consists of the following basic components assembled as miniature sub-units: a sample chamber, an X-ray source assembly, and an X-ray detector assembly. The sample chamber is substantially composed of a non-metallic material and has a cylindrical shape. The sample chamber is attached to the lubrication system of the machine such that the sample chamber provides a passageway through which the lubricant flows. The sample chamber has an X-ray transparent window, such as a beryllium window, formed therein that allows the passage of X-rays so that the presence of wear metal particles can be detected in the lubricant.

The X-ray fluorescence spectroscopy system also includes a high intensity, relatively small spot incident X-ray source assembly that is configured to provide a source of X-rays directed toward the sample chamber such that the X-rays pass through the window in the sample chamber and contact the lubricant flowing therethrough. The X-ray source assembly may comprise either an electron-beam excited X-ray tube and a collimating/focusing assembly, or, alternatively, an X-ray laser source.

The X-ray fluorescence spectroscopy system also incorporates an X-ray detector assembly that is configured to detect the X-rays emitted from the lubricant flowing through the sample chamber. The X-ray detector assembly generates a signal reflecting the X-rays emitted from the lubricant that is then processed to determine the presence and concentration of wear metal particles in the lubricant. The X-ray detector assembly comprises a collimator/focusing assembly capable of wide angle collection of the X-rays received from the lubricant flowing though the sample chamber, and a low-noise, high sensitivity X-ray detector.

The system utilizes a remote computer system and associated software for processing the signal in order to determine the presence and amount of wear metal particles in the lubricant. External to the compact X-ray fluorescence spectrometer system and assumed to be part of the main lubricated mechanical assembly is an oil pump and an electric power source. The results of wear metal content analysis are to be displayed in convenient form in an appropriate location.

These and other objects and features of the present invention will become more fully apparent from the following description and appended claims, or may be learned by the practice of the invention as set forth hereinafter.

BRIEF DESCRIPTION OF THE DRAWINGS

In order that the manner in which the above-recited and other advantages and objects of the invention are obtained, a more particular description of the invention briefly described above will be rendered by reference to specific embodiments thereof which are illustrated in the appended drawings. Understanding that these drawings depict only typical embodiments of the invention and are not therefore to be considered to be limiting of its scope, the invention will be described and explained with additional specificity and detail through the use of the accompanying drawings in which.

DETAILED DESCRIPTION OF THE PREFERRED EMBODIMENTS

The present invention provides a compact apparatus for performing an in-line X-ray fluorescence spectroscopy analysis and a method for using the same. The X-ray fluorescence spectroscopy system is miniaturized and in-line to provide a real-time analysis of a lubricant in a lubrication system of a machine. The X-ray fluorescence spectroscopy system excites a sample using X-rays and upon the energy from the sample decaying, a characteristic elemental X-ray emission is released that provides an identification of the presence and concentration of wear metal particles in the lubricant. Anticipated users of the X-ray fluorescence spectroscopy system include the military and civilian aircraft industry, spacecraft industry, automotive industry, and other industries employing a variety of lubricated moving parts and mechanisms.

Figure 1:
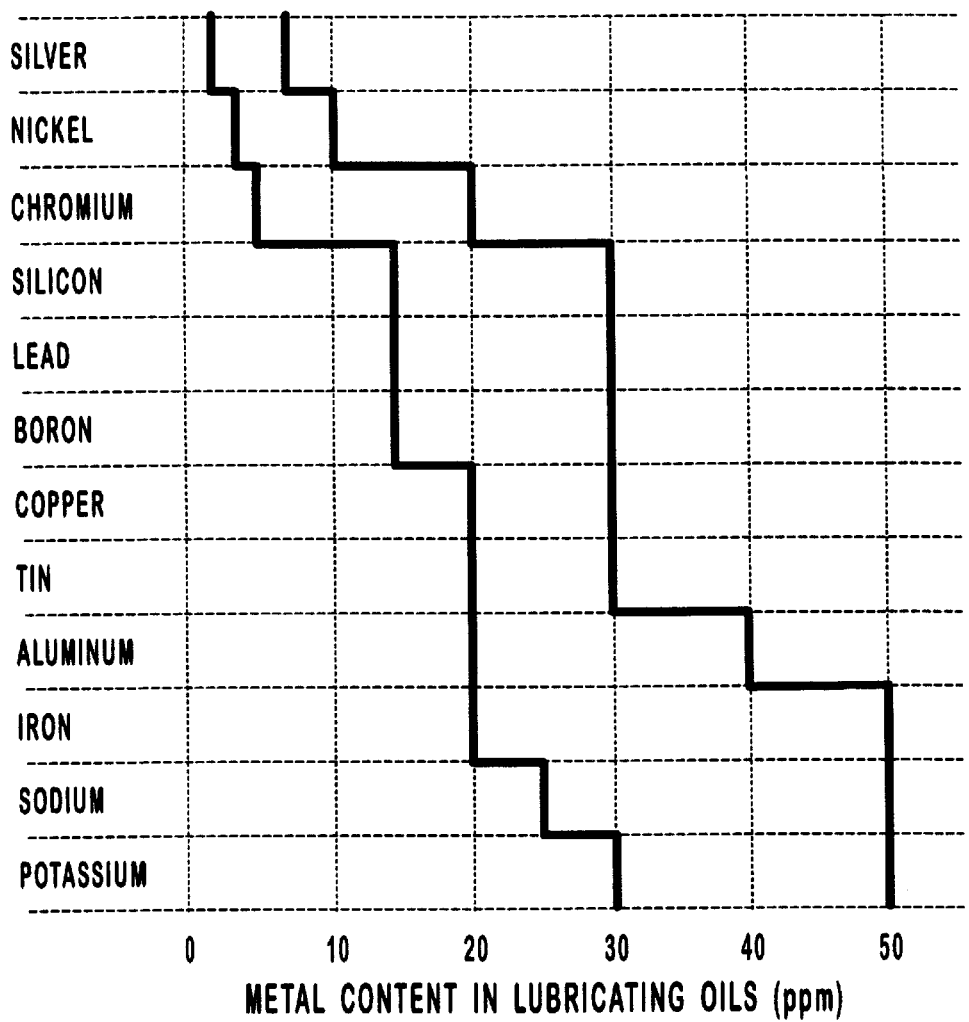
FIG. 1 is one example of an assessment chart for spectrographic oil.
Figure 2:
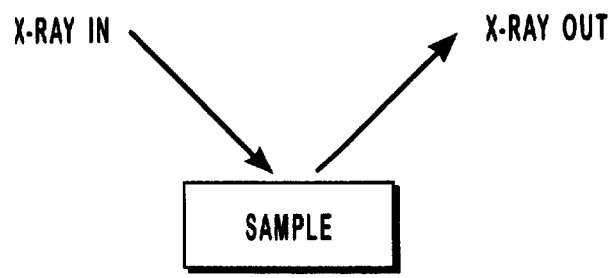
FIG. 2 is a schematic depiction of the two (2) stages of an X-ray fluorescence process.
Figure 3:
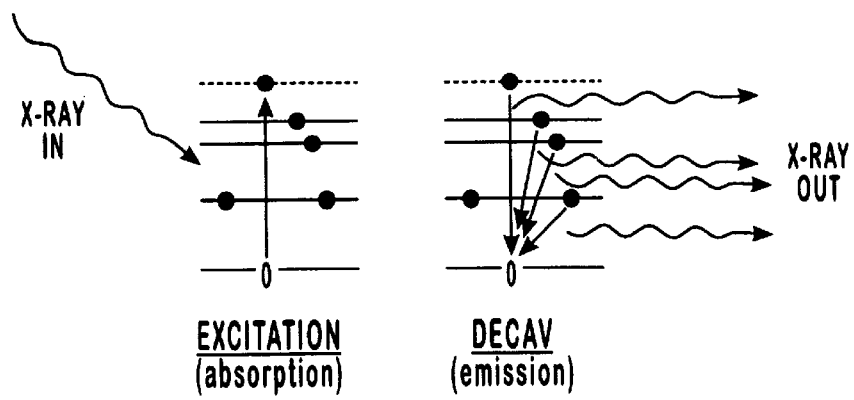
FIG. 3 illustrates the energy levels of a sample material as well as the absorption and the emission processes involved in the X-ray fluorescence process.
Figure 4:
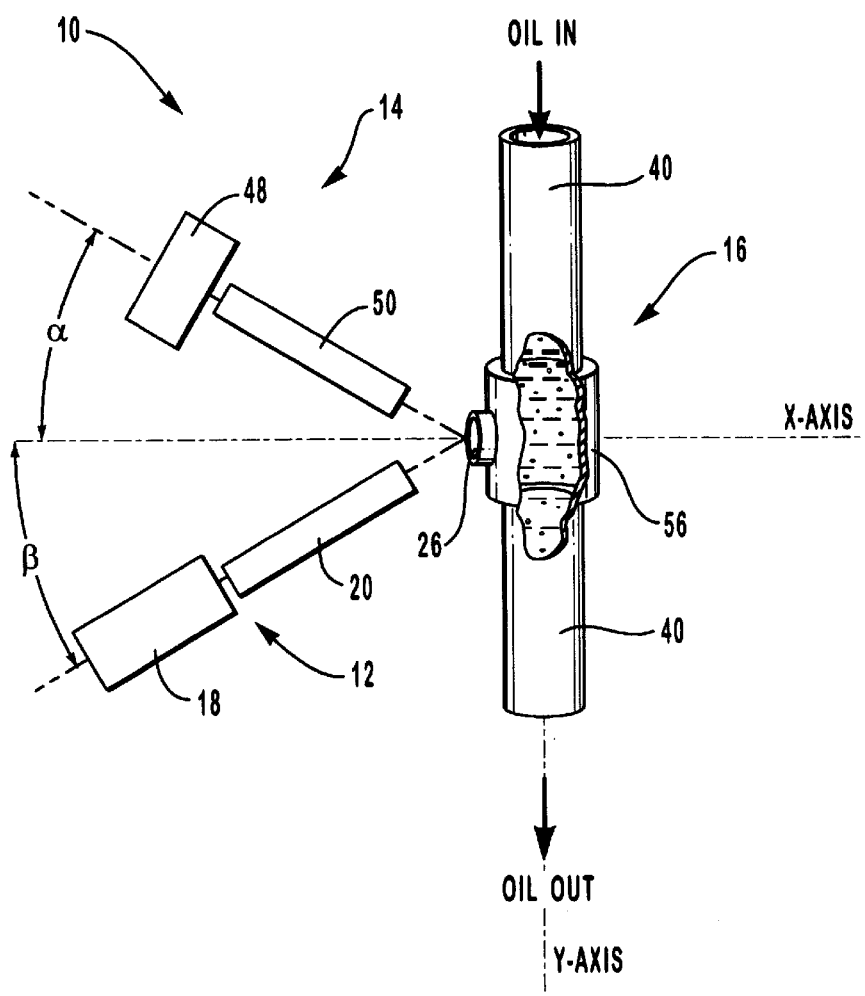
FIG. 4 is a schematic of one embodiment of a miniaturized X-ray fluorescence spectroscopy system.

One embodiment of a compact in-line X-ray fluorescence spectroscopy system is depicted generally at 10 in FIG. 4. X-ray fluorescence spectroscopy system 10 includes an X-ray source assembly 12, an X-ray detector assembly 14, and a sample chamber 16. X-ray source assembly 12, X-ray detector assembly 14, and sample chamber 16 can be referred to together as an excitation/emission/detection section. The overall size of this excitation/emission/detection section will be minimized to the extent permitted by the size of each modular component and the optimum geometric position of these components that assures a maximum operating performance.

As illustrated in FIG. 4, sample chamber 16 is tubular in shape and is adapted for in-line connection to a lubrication system such that sample chamber 16 provides a passageway through which the lubricant flows. Sample chamber 16 is concentrically inserted into main oil conduit 40 that transports the lubricant, such as oil, through the machinery that is being monitored for the presence of wear metal particles. Various other kinds of lubricants may be used in the lubrication system.

As depicted in FIG. 4, one embodiment of sample chamber 16 is substantially cylindrical in shape and oil circulates through sample chamber 16. Sample chamber 16 may also be referred to as a flow cell because the lubricant is moving through sample chamber 16. In one embodiment of X-ray fluorescence spectroscopy system 10 depicted in FIG. 4, the oil flow through sample chamber 16 is vertical in order to minimize the non-homogeneity of the suspension sample caused by possible gravitational sediment of wear metal particles in the case of a non-vertical flow path. It can be appreciated by those skilled in the art that in aircraft engine systems the oil flow direction will change during maneuvering of the aircraft. In other embodiments, sample chamber 16 may be connected in-line with the lubrication system such that the oil flow through sample chamber 16 has orientations other than vertical. The direction of oil flow through sample chamber 16 may be essentially irrelevant if the oil flowing through sample chamber 16 moves at a sufficient velocity such that any sedimentation effects are insignificant. In addition, in some machines, such as spacecraft, gravity is no longer a detrimental factor.

The inner diameter of sample chamber 16 is substantially equal to the inner diameter of the oil conduit 40 such that the velocity of the oil in main oil conduit 40 is preserved in sample chamber 16. Preserving the velocity of the oil through sample chamber 16 avoids any modification or false changes of the concentration of wear particles 56 suspended in the oil.

The composition of sample chamber 16 will be dependent on the specific application that X-ray fluorescence spectroscopy system 10 is being used for. The basic criteria for the selection of an appropriate material for sample chamber 16 are virtual total absorption of X-rays and good mechanical sturdiness. Sample chamber 16 may be substantially composed of non-metallic materials, such as, by way of example and not limitation, nylon, bakelite, or other appropriate plastic materials.

In the present instance, because only heavy metals are being monitored, sample chamber 16 can alternatively comprise light metals, such as by way of example and not limitation, aluminum or alloys thereof, with sufficiently high purities that sample chamber 16 does not generate X-ray signals that interfere with the signals of the heavy metal particles that represent contaminants in the lubricating oil. The preferred materials for sample chamber 16 are, however, non-metals.

Sample chamber 16 has a window 26 formed in the wall thereof. One embodiment of window 26, as depicted in FIG. 4, is circular. Window 26 may have various other configurations, such as elliptical or oval shapes, and differing sizes and perform the function thereof with equal effectiveness. The size of window 26 must be such that it can comfortably accommodate at its center the incoming X-ray beam emitted by X-ray source assembly 12 which has a relatively small size. The size of window 26 determines the amount of characteristic X-rays emitted by the sample that are allowed to exit sample chamber 16 and are collected by X-ray detector assembly 14. Accordingly, a larger window 26 results in a higher detected signal and, therefore, larger sensitivity.

Window 26 comprises an X-ray transparent material, such as, by way of example and not limitation, beryllium, KAPTON, boron, aluminum-coated polymers, or coated beryllium. The characteristics that are preferred in whatever material is used for window 26 are transparency to characteristic X-rays emitted by the element that is being monitored, such as the heavy metal elements in the present instance, ruggedness, chemical compatibility with typical lubricating materials, and temperature resistance. Where X-ray fluorescence spectroscopy system 10 is used with a chemically aggressive environment, such as one that is corrosive or oxidating, window 26 may comprise a chemically resistant coated beryllium foil window. In those cases where X-ray fluorescence spectroscopy system 10 is used in high temperature environments above 200° C. a special high temperature mounting for X-ray window 26 will be used.

KAPTON, the thin membrane used in the feasibility study discussed in Example 1 below, performed satisfactorily but at this time is generally not preferred because it is not sturdy enough to reliably seal window 26 in sample chamber 16 over a sufficiently long period of time. Should a KAPTON become available that is sturdier, it will perform the function of window 26 with acceptable effectiveness in specific applications. Therefore, at this time one preferred embodiment of window 26 in sample chamber 12 comprises a beryllium material.

The thickness of window 26 is chosen to meet the required intensity transmission of the X-rays combined with sturdiness and vacuum tightness. The thickness of window 26 is dependent on the design of X-ray fluorescence spectroscopy system 10 in order to optimize the performance of X-ray fluorescence spectroscopy system 10, and the type of mechanical assembly it is being used in. For example, where high detection sensitivity and/or low sample circulation velocity is needed window 26 will be thinner. In contrast, where a low detection sensitivity and/or a high sample circulation velocity is needed window 26 will be thicker.

Sample chamber 16 is one embodiment of a structure capable of performing the function of a sample chamber means for providing a chamber to measure the presence and amount of wear metal particles in a lubricant. The sample chamber means is adapted for in-line connection into the lubrication system so that the sample chamber means provides a passageway through which the lubricant flows.

Figure 8:
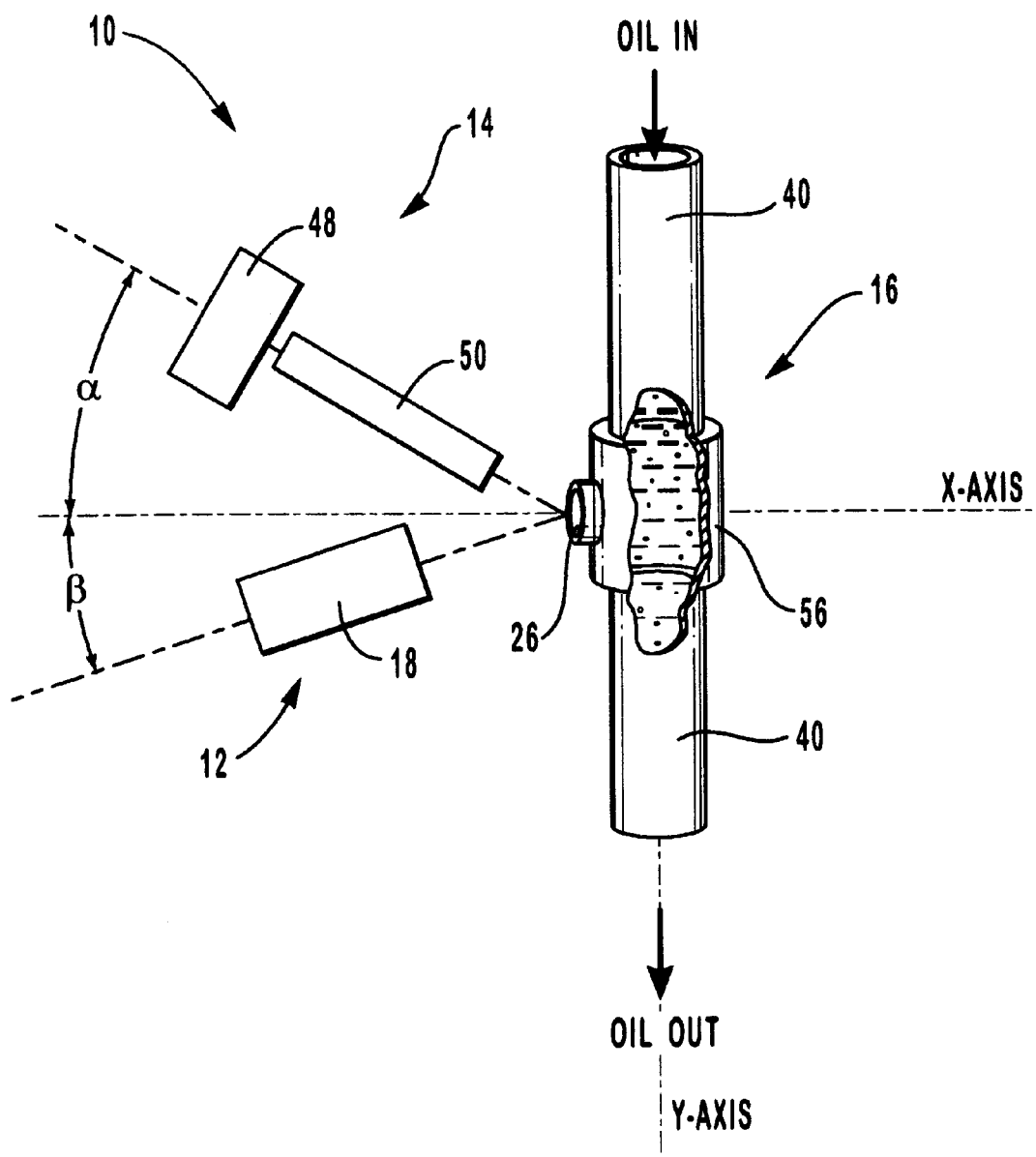
FIG. 8 is a schematic of an alternate embodiment of a miniaturized X-ray fluorescence spectroscopy system.

X-ray source assembly 12 is one embodiment of a structure capable of performing the function of a source means for providing a source of X-rays directed toward sample chamber 16 so that the X-rays pass into sample chamber 16 and contact the lubricant flowing therethrough. X-ray source assembly 12 may have two embodiments. In one embodiment depicted in FIG. 4, X-ray source assembly 12 comprises an X-ray tube 18 that utilizes electron beam excitation and a collimating/focusing assembly 20. Alternatively, another embodiment of X-ray source assembly 12 is shown in FIG. 8 and comprises an X-ray laser source 38.

Figure 5:
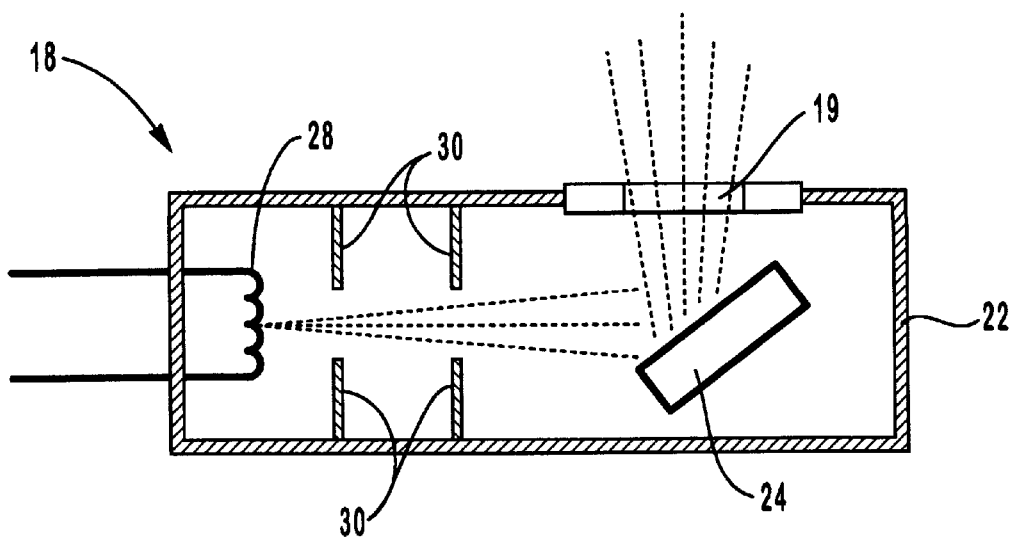
FIG. 5 is a cross-sectional view of one embodiment of an X-ray tube used in the X-ray fluorescence spectroscopy system of FIG. 4.

FIG. 5 illustrates one embodiment of X-ray tube 18 that is used in the embodiment of X-ray source assembly 12 depicted in FIG. 4. X-ray tube 18 is a small power, sealed, monochromatic, single anode X-ray tube. X-ray tube 18 includes an evacuated chamber 22 that houses the components of X-ray tube 18. X-ray tube 18 also comprises an anode target 24 and an X-ray tube window 19. One embodiment of anode target 24 comprises a substantially pure-metal rhodium anode target.

X-ray transparent window 19 of X-ray tube 18 must meet requirements very similar to those previously discussed relative to window 26 in sample chamber 16. X-ray 11 transparent window 19 must comprise a material that has good transparency for characteristic X-rays of heavy metals and have sufficient strength to maintain a vacuum within chamber 22 of X-ray tube 18. X-ray transparent window 19 is composed of material selected from the group consisting of beryllium, coated beryllium, KAPTON, and aluminum-coated polymers. As depicted in FIG. 5, X-ray transparent window 19 of X-ray tube 18 comprises a beryllium material.

X-ray tube 18 also comprises a heated electron emission filament 28. One embodiment of heated electron emission filament 28 is depicted in FIG. 5 has an adjustable current control. X-ray tube 18 also includes a set of accelerating electrodes 30 with adjustable high positive voltages. A filter (not shown) and an electronic interlocking system (not shown) can be used with X-ray tube 18. The filter comprises the same material as anode target 24 of X-ray tube 18, for example rhodium for bremsstrahlung radiation cut-off. The electronic interlocking system prevents accidental operator exposure to the X-rays.

X-ray tube 18 is constructed using a classic design that is familiar to those skilled in the art as well as having the most compact assembly size that is possible. One advantage of compact X-ray fluorescence spectroscopy system 10 is the fact that only detection of the $K_{\alpha 1}$ X-ray of iron at 6.4 keV is relevant, as opposed to X-ray tubes for general analytical laboratory scale X-ray fluorescence spectroscopy spectrometers in which a wide energy range for simultaneous detection of many elemental components is needed. Consequently, X-ray tube 18 has only one anode target 24 that is substantially composed of rhodium and a narrow range of accelerating voltages in the vicinity of the iron fluorescence emission, which is in this case 6.4 keV. The operation parameters of X-ray tube 18 are selected to have values close to the optimum values determined in the feasibility study discussed below in Example 1. Various further embodiments of X-ray tube 18 may be used and are equally effective in carrying out the intended function thereof. Obviously, embodiments designed to detect other primary wear materials or a broad range of wear materials may require adjustment of the basic design.

Figure 6:
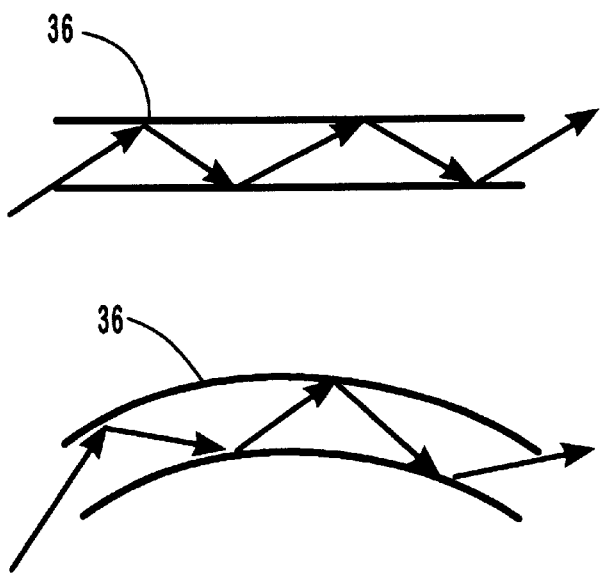
FIG. 6 depicts the path of X-rays through hollow capillary tubes with differing curvature.

In one embodiment of X-ray source assembly 12 that includes X-ray tube 18 as illustrated in FIG. 4, X-ray source assembly 12 also comprises an X-ray collimating/focusing assembly 20. Including X-ray collimating/focusing assembly 20 as part of X-ray fluorescence spectroscopy system 10 is a major factor that contributes to the high sensitivity performance thereof. One embodiment of X-ray collimating/focusing assembly 20 includes a bundle of thin, hollow capillary glass tubes 36. Capillary tubes 36 may be comprised of materials that may perform the function thereof with equal effectiveness. Capillary tubes 36 have a diameter in the range of about 5 microns to about 50 microns and are configured to control the path of the X-rays as illustrated in FIG. 6. X-ray fluorescence spectroscopy system 10 makes use of the total internal reflection of X-rays in capillary tubes 36 with an efficiency currently reported to be about 50%.

Figure 7:
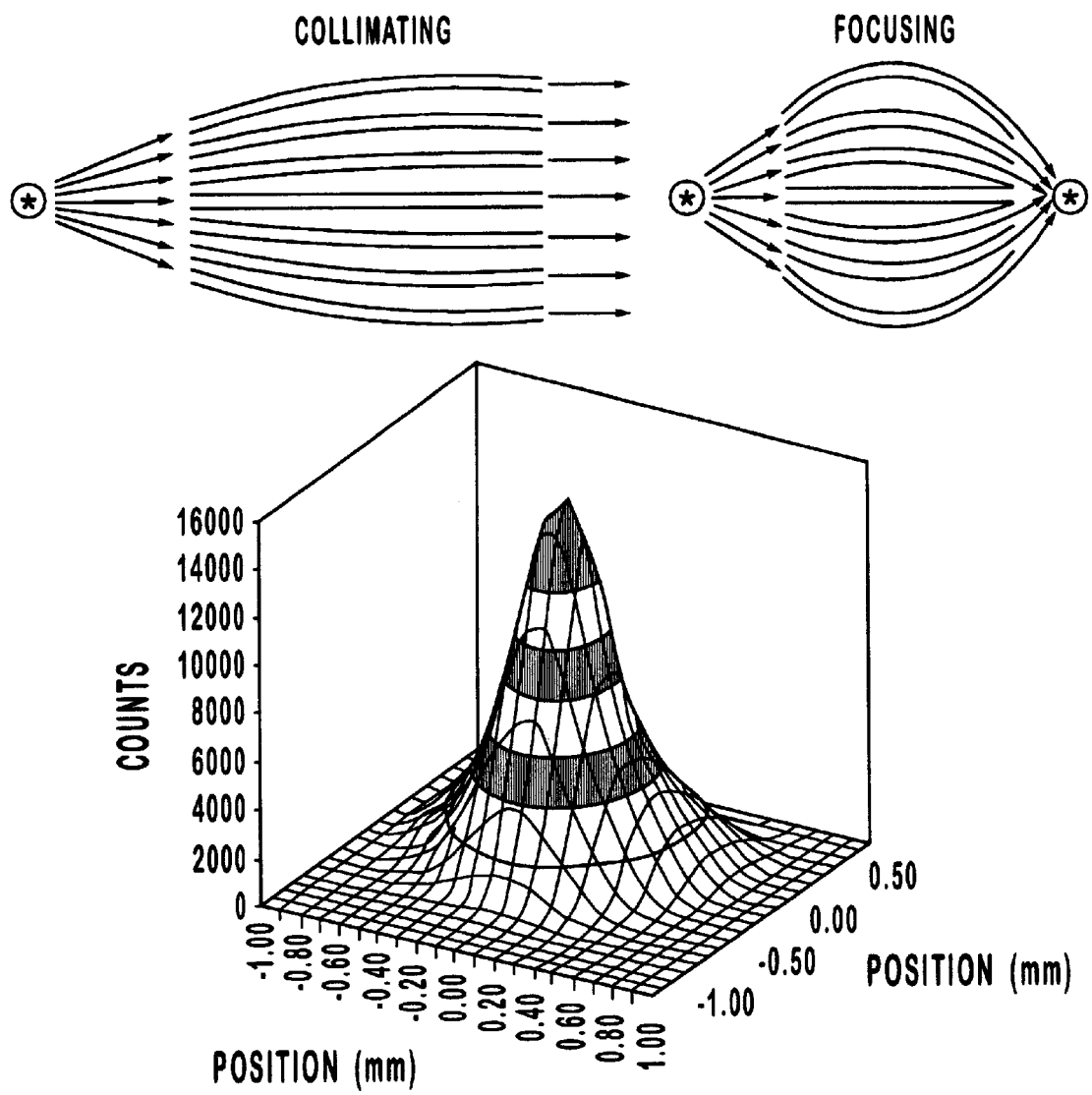
FIG. 7 depicts the collimation or focusing of X-rays by a one embodiment of a collimating/focusing assembly in the X-ray fluorescence spectroscopy system of FIG. 4.

As illustrated in FIGS. 6 and 7, hollow capillary tubes 36 collect the divergent X-ray beams emerging from a point source with a solid angle as large as 1 radian and either convert/collimate it into a parallel beams typically having a cross-sectional area of approximately 1 cm$^2$, or focus the X-ray beams into a "point" focus having a diameter of about 1 millimeter. Successfully operated systems utilizing capillary optics have had an X-ray energy range about 1 keV to about 60 keV. A preferable X-ray energy range is about 1 keV to about 30 keV. The X-ray energy range of interest for X-ray fluorescence spectroscopy system 10 that will be used to detect iron wear metal particles has a corresponding X-ray energy range for iron of about 6.4 keV and is well within the preferred energy range of X-ray source assembly 12.

In multifiber optics, a large number, such as several hundred, individual capillary tubes 36 are threaded through a frame of supporting screens that assure mechanical integrity and alignment. In monolithic optics, capillary tubes 36 are fused together and tapered, eliminating the need for an external supporting frame. The typical focal distances for commercially available constructions of these optical systems are about 100 mm to about 150 mm. In X-ray fluorescence spectroscopy system 10, both multifiber capillary systems and monolithic systems will be considered. In X-ray collimating/focusing assembly 20, optimum guidance of the X-ray beams is achieved by an appropriate selection of various properties of capillary tube 36 including but not limited to the material, diameter, wall smoothness, and bending profile of capillary tube 36.

An alternate embodiment of X-ray collimating/focusing assembly 20 comprises a block of low-density metal with a number of cylindrical holes having a submillimeter diameter bored therein. The block is substantially composed of materials selected from a group comprising aluminum and other potentially suitable "light metals". It is preferred that the block be substantially composed of aluminum. The number of cylindrical holes is typically a few dozen. In this embodiment, bending of the X-rays is achieved through multiple refractions at the concave metal-cavity interfaces inside the block of low-density metal. In most cases, focal spots having a diameter of approximately a micrometer can be obtained.

For the sample excitation stage in X-ray fluorescence spectroscopy system 10, very fine small spot focusing of the X-rays emitted by X-ray tube 36 is not necessary. The main goal is to collect an intense X-ray beam emitted by X-ray tube 36 at a wide solid angle, and to direct the beam toward an area of approximately 1 cm$^2$ to approximately 4 cm$^2$ of window 26 in sample chamber 16. The collimated/focused incident X-ray beam will enter into sample chamber 16 through window 26 and excite the circulating oil containing wear metal particles. Incorporating X-ray collimating/focusing assembly 20 into one embodiment of X-ray source assembly 12 that utilizes X-ray tube 18 as shown in FIGS. 4 and 5 produces a relatively small spot X-ray beam on window 26 in sample chamber 16 and eliminates any spurious signals generated by materials surrounding window 26 of sample chamber 16.

As previously mentioned, X-ray source assembly 12 may alternatively comprise X-ray laser source 38 shown in FIG. 8 instead of X-ray tube 18 and collimating/focusing assembly 20 illustrated in FIGS. 4 and 5. X-ray laser sources have been successfully developed in recent years. So far the energy of X-ray laser sources, however, extends only into the ultraviolet and the soft X-ray range with a wavelength of about 35 Å to about 300 Å. The current challenge is the developing of gamma ray lasers that involve transitions of charged particles within nuclear energy levels instead of electron transitions within the atomic energy levels.

The expected photon energies in gamma ray lasers is expected to span over a range of about 10 keV to about 100 keV which correspond to wavelength smaller than 1 Å. At this time, at least one isotope species is known. The known isotope species is an isotope of tantalum ($^{180}$Ta) that exists naturally in an excited state of 75 keV energy with a lifetime greater than 10$^{12}$ years. The present short term objective is to harness the release of this excess energy in the form of controllable gamma rays. It is contemplated that any of such X-ray laser sources 38 may be used with X-ray fluorescence spectroscopy system 10 illustrated in FIG. 8 as long as the energy and wavelength thereof are sufficient to detect the primary wear metal of interest. Methods of determining the proper energy and wavelength to detect the $K_\alpha$ line of the primary wear metal is known to one skilled in the art.

One embodiment of X-ray source assembly 12 that is shown in FIG. 8 and comprises X-ray laser source 38 does not require focusing/collimating because X-ray laser source 38 provides a small spot beam with insignificant divergence over the entire short distance between X-ray source assembly 12 and window 26 as designed in the compact X-ray fluorescence spectroscopy system 10.

X-ray fluorescence spectroscopy system 10 also includes X-ray detector assembly 14 depicted in FIGS. 4 and 8. X-ray detector assembly 14 is one embodiment of structure capable of performing the function of a detector means for detecting the X-rays emitted from the lubricant flowing through sample chamber 16. The detector means generates a signal reflecting the X-rays emitted from the lubricant.

Figure 9:
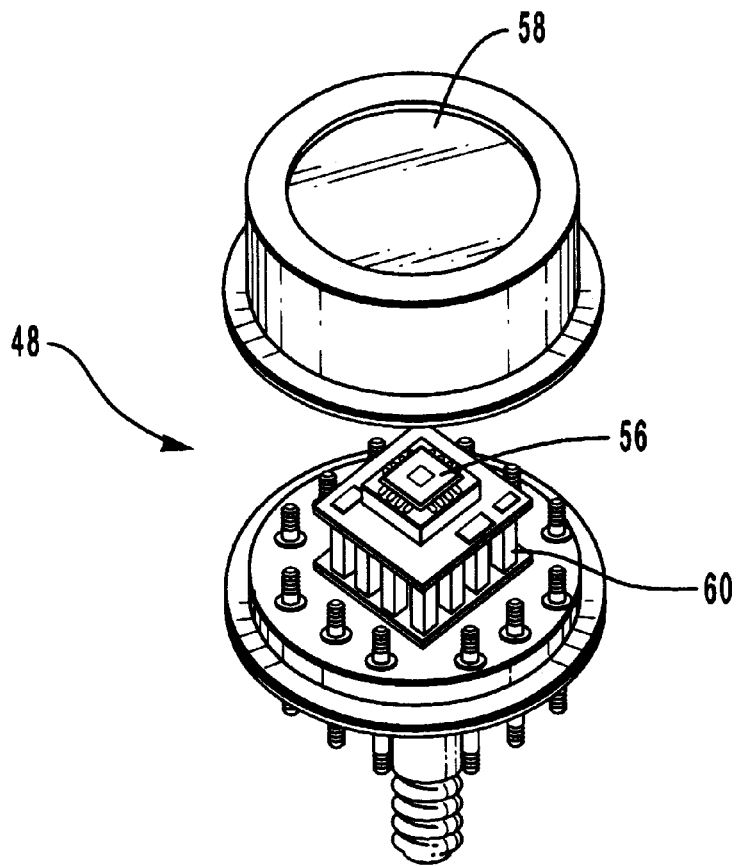
FIG. 9 is a partially exploded perspective view of one embodiment of an X-ray detector and an example of the results that are received from the detector.
Figure 9:
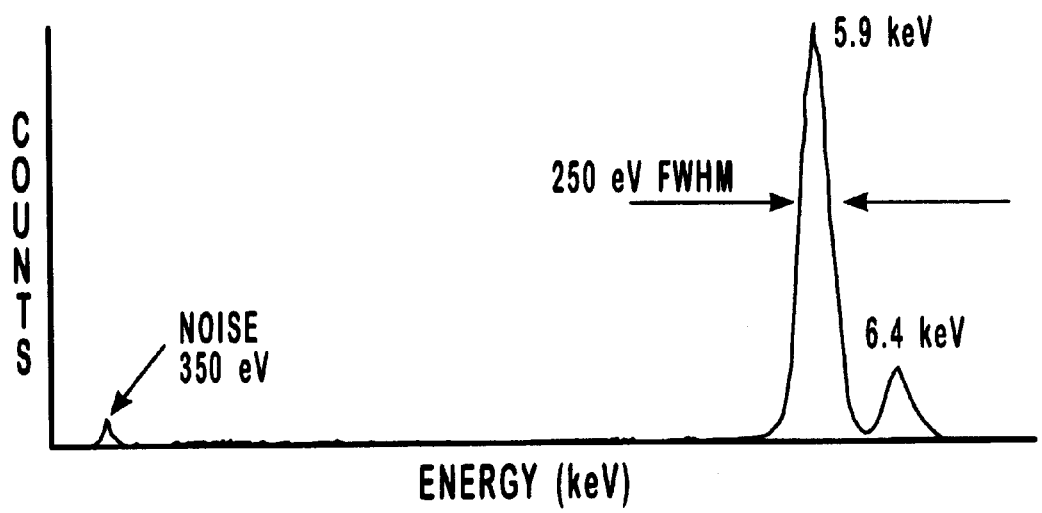

X-ray detector assembly 14 comprises an X-ray detector 48 as shown in FIG. 4. X-ray detector 48 may have various embodiments and still perform the function thereof with equal effectiveness. One embodiment of X-ray detector 48 is depicted in FIG. 9 and is a low-noise detector. Detector 48 has an X-ray transparent window 58 formed therein that must meet requirements very similar to those previously discussed relative X-ray tube window 19. X-ray transparent window 58 comprises an X-ray transparent material, such as, by way of example and not limitation, beryllium, coated beryllium, KAPTON, boron, and aluminum-coated polymers. The characteristics that are preferred in whatever material is used for window 58 are transparency to characteristic X-rays emitted by the lubricant and the ability to maintain vacuum tightness.

In the embodiment depicted in FIG. 9, window 58 comprises beryllium. Detector 48 comprises a Si-PIN photodiode 56, a light-tight, vacuum-tight window 58, and uses a thermoelectric cooling 60 and a feedback circuit (not shown). One embodiment of low-noise detector 48 is a low-noise lithium silicon detector. Detector 48 operates at a constant temperature of approximately 30° C., and has an energy resolution of 250 eV Full Width at Half Maximum (FWHM) at 5.9 keV. The noise level is of the order of 3×10$^{-3}$/sec over the 2 keV to 150 keV energy range. The power supply (not shown) for X-ray detector 48 can be installed in a location remote from X-ray detector assembly and is capable of ensuring quick, stable detector operation in less than one minute from power turn-on. As depicted in FIG. 9, the height of the spike is proportional to the concentration of wear metal particles.

X-ray detector assembly 14 also includes a focusing/collimating assembly 50. As depicted in FIGS. 4 and 8, focusing/collimating assembly 50 is positioned between sample chamber 16 and X-ray detector 48. In X-ray fluorescence spectroscopy system 10, the fluorescent X-rays emitted over a wide solid angle by the oil specimen will be concentrated by either a collimating or focusing process on beryllium window 58 of detector 48. This results in a superior performance of X-ray fluorescence spectroscopy system 10 in terms of sensitivity and fast detection response. X-ray collimating/focusing assembly 50 is similar in principle to collimating/focusing assembly 20 shown in FIG. 4, that is designed for collimating/focusing of the X-ray beam emitted by X-ray tube 18 incident on the oil sample.

Figure 10:
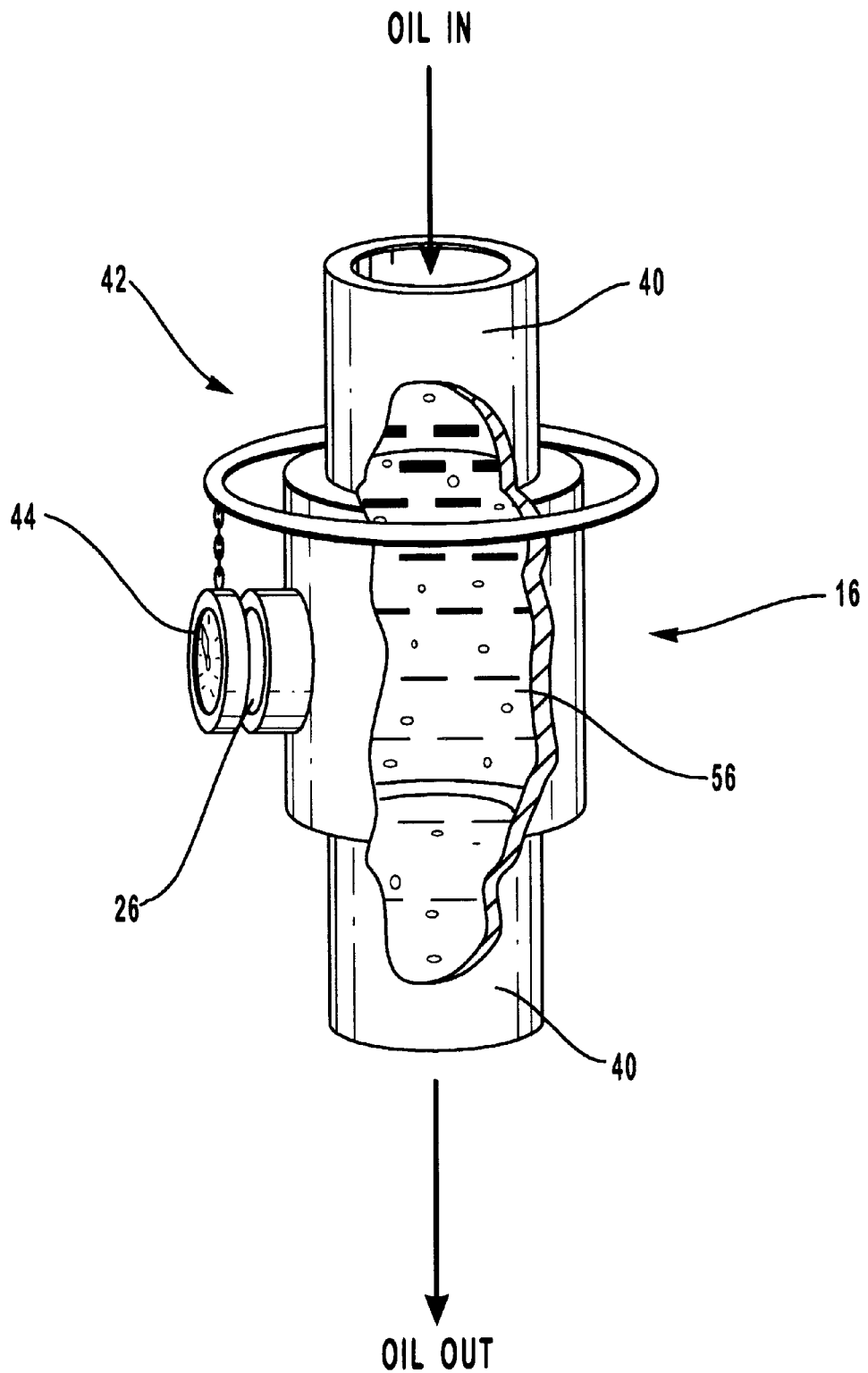
FIG. 10 is a partial break-away perspective view of one embodiment of a sample chamber and a calibration disk mechanism.
Figure 12:
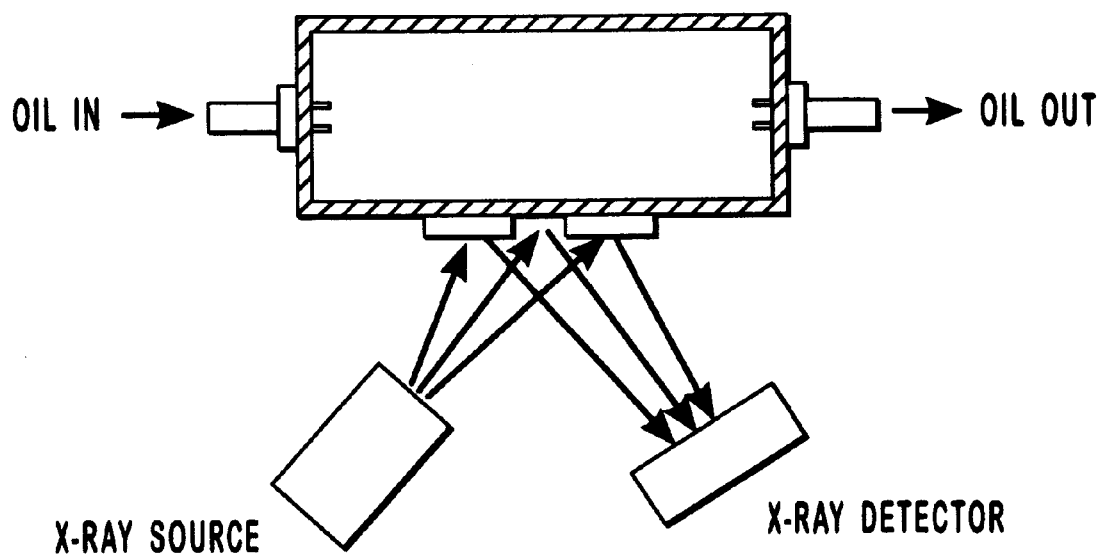
FIG. 12 illustrates the geometry of the X-ray fluorescence spectroscopy system of FIG. 11.

X-ray fluorescence spectroscopy system 10 also includes a calibration system 42 that is movably positioned over sample chamber 16 as depicted in FIG. 12. Calibration system 42 comprises a calibration sample 44 that is movably positioned in front of window 26 of sample chamber 16. One embodiment of calibration sample 44 comprises a copper disk that is mounted on a movable frame 45 and is positioned in front of window 26 in sample chamber 16 as shown in FIG. 10. Calibration system 42 is configured to include a moving mechanism (not shown) that brings calibration sample 44 in front of sample chamber window 26, and then removes calibration sample 44 after the energy calibration is completed. The moving mechanism is operated by the machine operator, such as the pilot, from a convenient remote location such as an aircraft cockpit. Details on the design, construction, and operation of this mechanism are not critical for operation of this invention. It is, however, important that X-ray fluorescence spectroscopy system 10 be properly calibrated.

In one embodiment of calibration system 42, calibration sample 44 comprises a solid copper disk. Calibration sample 44 may have various embodiments and comprise other substantially pure chemical elements. Calibration sample 44 comprises a material that emits an X-ray line suitable for calibration of the $K_{\alpha 1}$ X-ray of the material that is being studied. Therefore, when heavy metals, such as iron in this case, are being measured, copper is to be used as calibration sample 44. Calibration sample 44 and the moving mechanism are one embodiment of a structure capable of preforming the function of a calibration means for calibrating the instruments in X-ray fluorescence spectroscopy system 10.

The embodiments of X-ray source assembly 12 and X-ray detector assembly 14 are geometrically positioned as shown in FIGS. 4 and 8. X-ray source assembly 12 and X-ray detector assembly 14 are positioned laterally with respect to the longitudinal or y-axis of sample chamber 16 and are on the same side of sample chamber 16 as window 26 formed therein. X-ray source assembly 12 and X-ray detector assembly 14 are positioned on opposing sides of an x-axis that passes through the center of windows 26 of sample chamber 16 and is perpendicular to the plane of window 26 and to the longitudinal or y-axis of sample chamber 16. Assembly 14 is positioned at an X-ray source angle β from x-axis and X-ray detector assembly 14 is positioned at an angle α from x-axis.

In one embodiment, depicted in FIG. 4, X-ray source assembly 12 and X-ray detector assembly 14 are positioned at an angle β and an angle α from the x-axis, respectively. In one embodiment in FIG. 4, α and β are substantially equal. It is contemplated, however, that X-ray assembly 12 and X-ray detector assembly 14 may be at differing angular positions, and are not symmetric about the x-axis. FIG. 8, by way of example and not limitation, illustrates an alternate geometric arrangement of X-ray source assembly 12 and X-ray detector assembly 14.

In addition, X-ray source assembly 12 and X-ray detector assembly 14 are positioned at varying distances from the longitudinal or y-axis of sample chamber 16 and, consequently, window 26 in sample chamber 16, in order to assure collimating/focusing of the incident X-ray beam on window 26 and collimating/focusing of the emitted X-ray beam from the lubricant window 58 of detector 48. X-ray source assembly 12 and X-ray detector assembly 14 can each be positioned at varying distances from longitudinal or y-axis as shown in FIGS. 4 and 8. X-ray source assembly 12 and X-ray detector assembly 14 are not required to be the same distance from longitudinal or y-axis of sample chamber 16. In any case, the positioning of X-ray source assembly 12 and X-ray detector assembly 14 is such that calibration sample 42 can be placed in front of and removed from window 26 of sample chamber 16 to permit focusing of incident X-ray beam on calibration sample 44 on windows 58 of detector 48 for calibration purposes.

A number of components listed below have auxiliary functions and are chosen as either dedicated commercially available units, or are used as units "borrowed" from the main machine or mechanism for the purposes of operation of X-ray fluorescence spectroscopy system 10. It is assumed that some of these components have been incorporated as intrinsic components of the general lubricated system, machine, or mechanism, such as engines for aircraft, helicopters, space craft, submarines, automobiles, and industrial installations. The size, weight, volume, and/or geometric configuration of these auxiliary components may be dictated by the optimum design of the general system, machine, or mechanism, and, as such, may be considered as either irrelevant for the purposes of the present invention, non-optional or non-selectable. These auxiliary components include the oil pump, the main oil flow conduit, the computer, the printer, the electric power supply unit and the data display instruments.

Miniaturization of as many components as possible is desirable, especially in mobile systems or in systems for which lifting and carrying of large and/or heavy loads is an issue such as, by way of example and not limitation, aircraft, space craft, and submarines. However, the auxiliary components do not impose any specific stringent size, weight, volume, or geometric disposition or restrictions on the proposed X-ray fluorescence spectroscopy system 10.

X-ray fluorescence spectroscopy system 10 includes a pump and a power source. Since sample chamber 16 is inserted in the main oil flow system, the same pump that circulates the lubricating oil through the lubrication system of the machinery also circulates the oil through sample chamber 16. A power source is necessary for X-ray source assembly 12 and X-ray detector assembly 14 of X-ray fluorescence spectroscopy system 10 and can either be acquired from the commercially available systems or can be specifically designed for a particular application. Optimally, the power source heats filament 28 of X-ray tube 36 and applies accelerating voltage for electron bombardment of rhodium anode target 24 in embodiment of X-ray source assembly 12 that includes X-ray tube 18 as shown in FIG. 4, or, alternatively, activates and operates X-ray laser source 38 in another embodiment of X-ray source assembly 12 as depicted in FIG. 8. Other power needs are provided separately by the auxiliary units. The additional power requirements include providing power to the oil pump of the machine, providing operating power to the computer for data processing, and providing power to the moving mechanism of calibration system 42.

A computer can be assembled from commercially available components and programmed to perform the tasks related to X-ray fluorescence spectroscopy system 10 and to perform the necessary data processing. Alternatively, special purpose computers designed specifically to accomplish one or more tasks can also be used. The tasks to be performed by the computer or computers include activating X-ray source assembly 12, manipulating calibration system 42, setting measurement parameters, initiating energy calibration using calibration system 42 controlling X-ray detector assembly 14, collecting fluorescent X-ray intensity data, subtracting background data, converting fluorescent X-ray intensity data into ppm concentration values, operating safety interlocking mechanisms, and other signal processing or control operations. The computer and accompanying programs are one embodiment of a structure capable of performing the function of a means for processing the signal from X-ray detector assembly 14 in order to determine the presence and amount of wear metal particles in the lubricant.

It is anticipated that the present invention will operate with unique performance characteristics never before possible, in terms of speed, sensitivity, and effectiveness of wear metal detection, as well as cost and safety. Miniaturizing the modular units as well as the entire X-ray fluorescence spectroscopy system 10 and inserting the X-ray fluorescence spectroscopy system 10 in-line with the lubrication system of the machine for on-line and real time inspection of wear metal particles makes the improved performance possible. In particular sample chamber 16, the X-ray source assembly 12, the X-ray detector assembly 14, and calibration system 42 have been miniaturized. Collimating/focusing assembly 20 for the incident X-ray beam in the embodiment of X-ray source assembly 12 with X-ray tube 18 has been miniaturized. In addition, collimating/focusing assembly 50 of the emitted fluorescent X-ray beam in X-ray detector assembly 14 has been miniaturized.

The improved X-ray fluorescence spectroscopy system 10 has an increased incident beam intensity interacting with the sample due to the high output of the capillary tubes 36 in one embodiment of focusing/collimating assembly 20 used with X-ray tube 18 in the embodiment of X-ray fluorescence spectroscopy 10 depicted in FIG. 4, or in the alternate embodiment of X-ray source assembly 12 shown in FIG. 8 that comprises X-ray laser source 38 that generates a high intensity X-ray beam. In either case, the sensitivity of the instrument and signal-to-noise ratio are increased. It should be mentioned that, although collimating/focusing assembly 20 with capillary tubes 36 has a limited optical transmission efficiency, it is anticipated that this will result in a significant increase in beam intensity at window 26 of sample chamber 16 compared to non-collimated or non-focused X-ray sources used in currently available X-ray fluorescence spectroscopies, due to collection of X-rays emitted by X-ray tube 18 within a wide solid angle. The increase in sensitivity also results in a significant decrease in the measurement time and the time response of X-ray fluorescence spectroscopy system 10.

X-ray fluorescence spectroscopy system 10 is able to do large solid angle collection of emitted X-rays, due to focusing of the X-rays emitted by the sample over a wide solid angle on X-ray detector assembly 14. The use of a non-metal sample chamber 16 eliminates spurious iron signals and thus decreases the spectral background and enhances the signal to background ratio. The use of a small volume, cylindrical, in-line sample chamber 16 diminishes the risk of modifying the concentration of wear particle in oil samples possibly caused in large, parallelipipedic, out-of-line types of sample chambers by formation of vortices, accumulation of solid particles in stagnation regions such as chamber corners or gravitational sedimentation. The improved X-ray fluorescence spectroscopy system 10 instrument will be operated over a restricted energy range such as one characteristic only for iron as the dominant wear metal component. Although in this application X-ray fluorescence spectroscopy system 10 is used only in the 6.4 keV range to detect iron wear metal particles, it is anticipated and intended that X-ray fluorescence spectroscopy system 10 may be used in other ranges to detect other elements. The improved X-ray fluorescence spectroscopy system 10 utilizes smaller, lower cost, and safer X-ray source assemblies 12.

EXAMPLE NO. 1

Laboratory-Scale Feasibility Study in a Simulated On-Line Wear Metal Analysis of Lubricating Oils.

Figure 11:
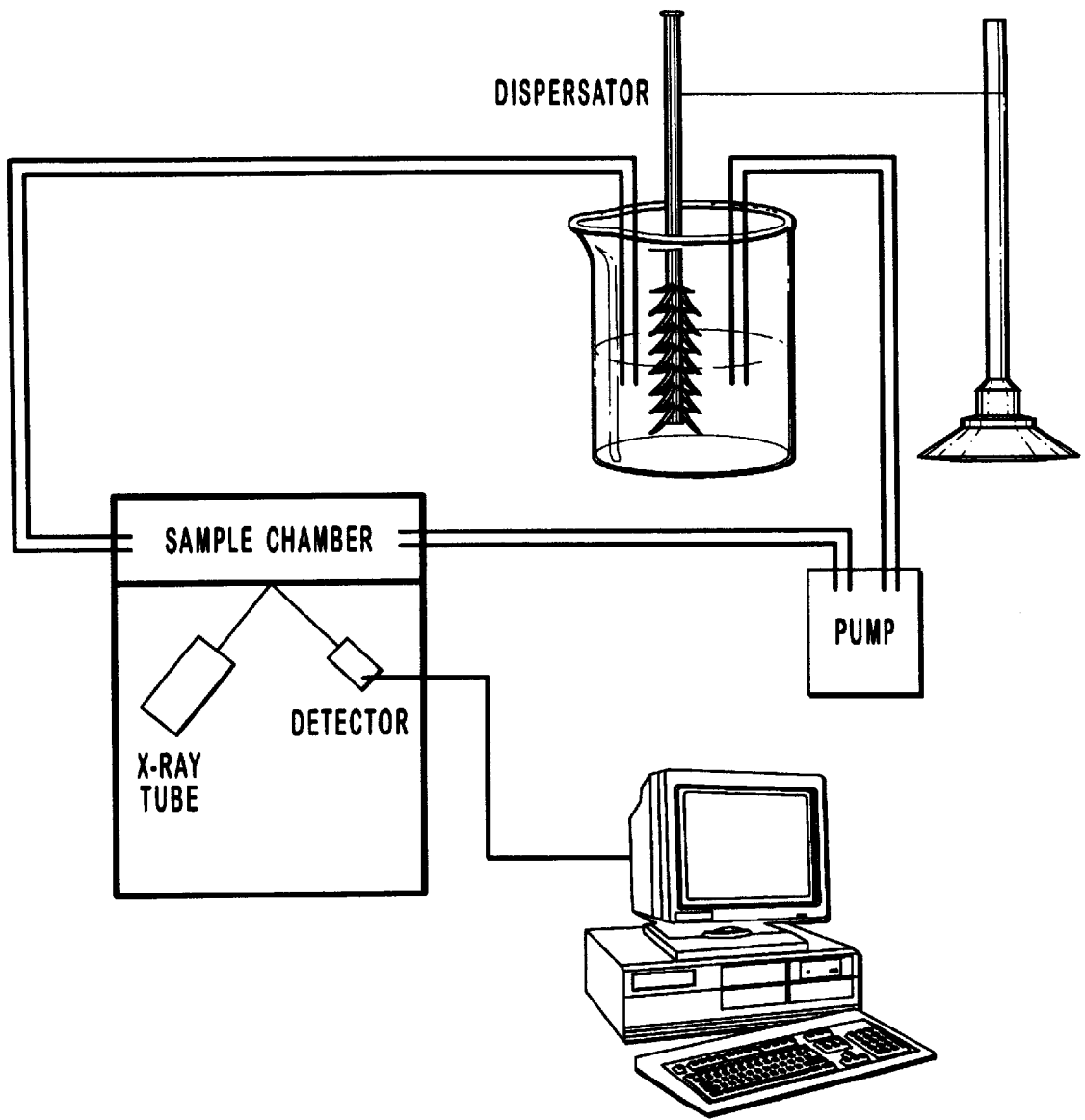
FIG. 11 is a schematic diagram of one embodiment of the X-ray fluorescence spectroscopy system used in a feasibility study.

The feasibility of using the X-ray fluorescence spectroscopy for qualitative and quantitative evaluation of wear metal particles in engine oil suspensions, and the feasibility of real-time dynamic wear metal analysis were demonstrated in the laboratory. The experimental set-up used in this feasibility study consisted of: (1) a commercial (SPECTRACE 6000) X-ray fluorescence spectrometer containing an X-ray source, an X-ray detector, and two (2) interchangeable sample chambers; (2) an oil sample reservoir equipped with an axial electric dispersator; (3) a pump for liquid sample circulation; and (4) a computer for data analysis. The interchangeable sample chambers were a static sample chamber and a flow-cell sample chamber. A schematic diagram of the arrangement of the equipment is shown in FIG. 11. As depicted in FIGS. 11 and 12, in the SPECTRACE 6000 instrument, both the X-ray tube and the detector were positioned underneath the sample chamber and were in a 90° line geometric configuration with each other as shown.

The X-ray tube was the type that was excited by high energy electron bombardment. The X-ray tube had a rhodium target anode and a beryllium window. The X-ray tube could deliver X-ray energy in the range of 6 keV to 50 keV and current in the range of 0 mA to 0.35 mA. The types of filters that were used with the X-ray tube were aluminum, rhodium thin, rhodium thick, copper, and cellulose. The X-ray tube also had a non-focused X-ray beam with an optional cylindrical collimator.

The X-ray detector was an all solid lithium drifted silicon detector with an area of 20 $mm^2$. The X-ray detector was cooled by a thermoelectric system. The resolution of the X-ray detector was 195 eV at 5.9 keV.

As previously mentioned, the X-ray fluorescence spectrometer was equipped with two interchangeable assemblies for static and dynamic sample analysis. Static samples were contained in plastic cups positioned underneath an X-ray shielding lid at the top of the spectrometer. For circulating samples, the shielding lid was replaced by a flow-cell or sample chamber assembly. The direction of oil flow through the sample chamber assembly was horizontal. The flow cell was made of stainless steel. In the flow cell, KAPTON membranes were used as X-ray transparent windows. For an immediate improvement of the instrument performance, in order to mask the stainless steel area surrounding the KAPTON window, collars of nylon or bakelite were installed.

For calibration, a copper disk was placed manually in the same position as the 11 bottom of the plastic cups containing the oil samples used for the static X-ray fluorescence spectroscopy analysis. After calibration, the calibration disk was manually removed.

Oil suspension samples of typically 250 ml were prepared in a 500 ml glass reservoir connected through plastic tubing to the X-ray fluorescence spectroscopy sample chamber by a MasterFlex peristaltic pump with a digital console drive as depicted in FIG. 11. The oil samples were homogenized in the glass container by using a vertical axis electric dispersator.

Four (4) sets of oil samples were studied. The first oil sample was pure DTE oil. Solutions of Fe-organometallic standard in DTE oil, with concentrations from 5 ppm to 5,000 ppm. were used as the second oil sample. The third oil sample consisted of suspensions of high purity spherical iron particles of 2 microns, 4 microns, and 8 microns diameter in DTE oil, with concentrations from about 5 ppm to about 5,000 ppm. The third oil sample also contained minute amounts, ~1%, of a dispersant additive. The fourth oil sample was from real contaminated oil samples collected from Langley Air Force Base aircraft engines and gear boxes, NASA Langley Research Center wind tunnels, and Langley Aero Club aircraft engines.

This study was focused on iron as the majority wear metal component. For energy calibration of the X-ray fluorescence spectroscopy system, the $K_{\alpha 1}$-emission line of copper at 8.048 keV was used. The variable experimental parameters were: particle size, particle concentration, and oil velocity. The X-ray fluorescence spectroscopy spectra were measured for both static samples with the samples in plastic cups and circulating dynamic samples.

The measurement parameters were optimized to provide maximum detected X-ray intensity, and are shown in Table 1:

TABLE 1

| | |
|---|---|
| X-ray tube filter: | Rhodium thin |
| Tube voltage: | 31 kV |
| Current: | 0.23 mA |
| Live collection time: | 1,000 sec. |

TABLE 1-continued

| | |
|---|---|
| Dead time: | ~50% |
| Oil speed: | 700 ml./min. |
| Calibration Line: | Copper |

Figure 13:
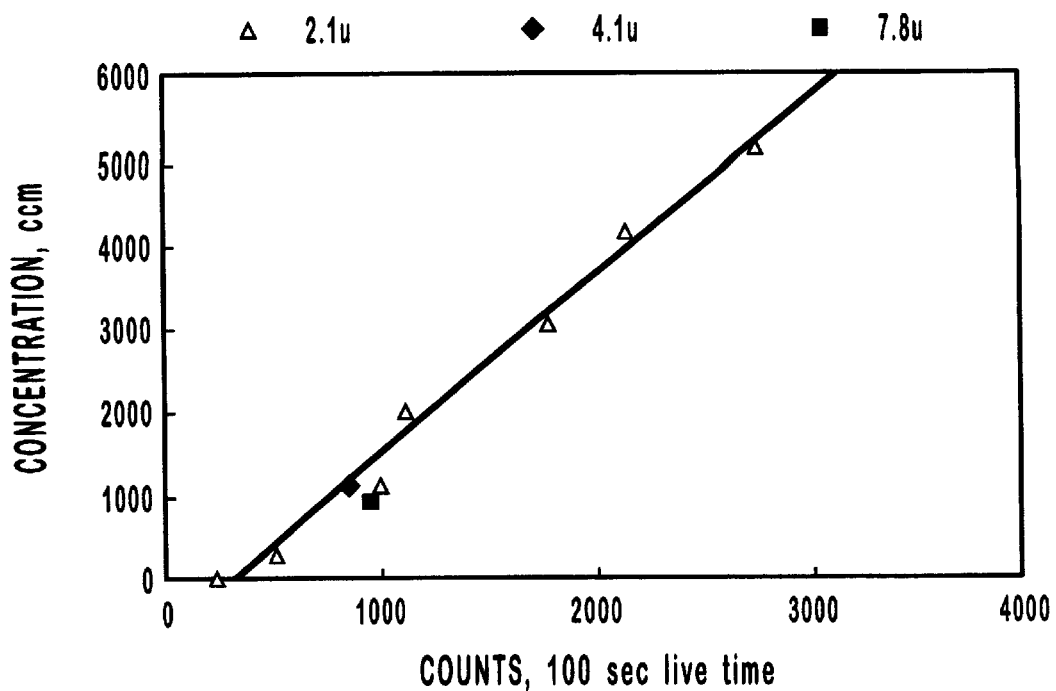
FIG. 13 is a graphic depiction of the intensity of Fe—$K_{\alpha 1}$ line as a function of suspended Fe particle size.
Figure 14:
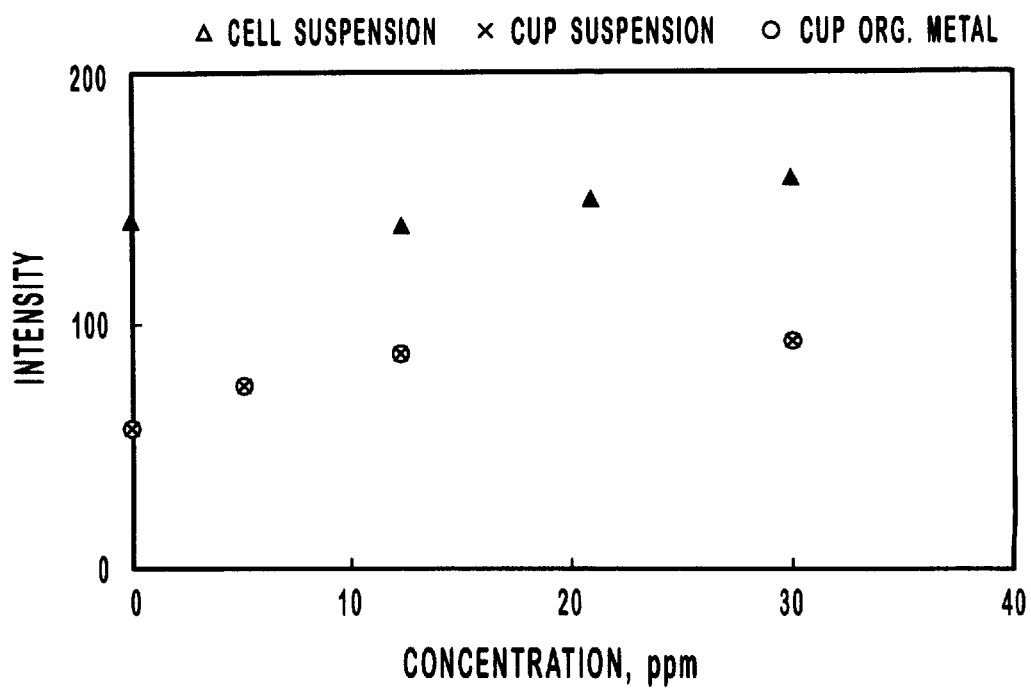
FIG. 14 is a graph comparing the data for standard organo-Fe solutions and for flowing suspension samples.

Good reproducibility of data was obtained at the selected optimum operation parameters, both for iron-organometallic solutions and for oil suspensions. FIG. 13 shows a linearly increasing intensity of the Fe—$K_{\alpha 1}$ line with increasing particle concentration for oil suspension samples with various particle sizes. This trend indicated that a reliable quantitative analysis of oil suspensions is possible. FIG. 14 is a comparison between the data obtained for static organo-Fe standard solutions and for flowing suspension samples. Again, good quantitative data was obtained that showed practically the same iron $K_{\alpha 1}$ line intensity for both the standard organometallic solutions and for the oil suspensions.

It was, however, determined that the SPECTRACE 6000 Instrument had several inadequacies. From the beginning, a number of intrinsic inadequacies of the commercial instrument that was used were recognized and revealed relative to its capabilities to meet the specific requirements of the laboratory scale feasibility study. The X-ray tube provided a divergent X-ray beam which, at the position of the sample, could "see" an area larger than that defined by the KAPTON window of the sample chamber depicted in FIG. 12. This resulted in a large iron background signal belonging to the steel wall of the sample chamber, and, consequently, a small signal-to background ratio, especially at low particle concentrations. In order to eliminate this problem, the sample chamber area surrounding the KAPTON window was masked with nylon or bakelite collars.

Because of the divergence of the incident X-ray beam, only a limited beam intensity entered the KAPTON window and effectively excited the oil sample. Consequently, the spectrometer had a low signal-to-noise ratio and, therefore, a marginal sensitivity at very low particle concentrations such as in the range of 1 ppm to 10 ppm for example, which represents exactly the region of interest. Because of the low X-ray beam intensity, a large data collection time of 1,000 seconds was needed. The instrument geometry, with the sample cell positioned above both the X-ray tube and the detector as depicted in FIG. 11, posed the problem of possible accumulation or sedimentation of suspended particles at the site of the KAPTON window, which could modify the concentration of the sampled volume and alter the experimental data. These effects are due at least in part to the gravitational effects on the particles. No simple solution was available to eliminate this problem in the factory fixed instrumental set-up.

For the purpose of this experiment, a thin membrane comprising KAPTON was used as a window and performed satisfactorily but is generally not preferred because at this time it is not sturdy enough to reliably seal the window in the sample chamber over a sufficiently long period of time. At such a time as that a sufficiently thick window comprising KAPTON can be made the KAPTON window will perform the function of an X-ray transparent window with equal effectiveness.

Finally, the sample flow-cell was too large for the needs of the feasibility study. Since stirring or any other method for sample homogenization were not possible in the sample chamber, an enhancement of the gravitational effect mentioned above could occur during filling of the large volume of the flow cell. In order to minimize this effect, a large sample pumping speed was chosen.

Based on the laboratory scale study it was determined that the X-ray fluorescence spectroscopy system is sensitive to flowing samples of iron particles suspended in lubricating oil, in the low concentration range of interest for early detection of risks of catastrophic mechanism failure. Both qualitative and quantitative reliable real-time X-ray fluorescence spectroscopy analyses of solid iron particles with typically micron size, suspended in flowing lubrication oil, are possible.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. An apparatus for measurement of wear metal particles in a lubricant of a lubrication system of a machine, said apparatus comprising:

(a) a sample chamber means for providing a chamber to measure the presence and amount of wear metal particles in said lubricant, said sample chamber means adapted for in-line connection into the lubrication system so that said sample chamber means provides a passageway through which the lubricant flows, at least a portion of said sample chamber means allowing passage of X-rays into and out of said sample chamber means so that the presence of wear metal particles can be detected in the lubricant;

(b) source means for providing a source of said X-rays directed toward said sample chamber means so that said X-rays pass through said sample chamber means and contact the lubricant, and metal particles that the lubricant may contain, flowing therethrough;

(c) detector means for detecting said X-rays emitted by the lubricants and by metal particles that may be contained therein, as the lubricant and metal particles flow through said sample chamber means, said detector means generating a signal representing a quantitative measure of said X-rays emitted by the lubricant and said X-rays emitted by the metal particles; and (d) means for processing said signal in order to determine the presence and amount of wear metal particles in the lubricant, thereby providing real-time identification and measurement of wear metal particles in the lubricant.

2. A compact apparatus as recited in claim 1, wherein said sample chamber means comprises a tubular sample chamber configured for in-line connection to said lubrication system, said sample chamber having a longitudinal axis substantially parallel to the flow of said lubricant therethrough.

3. A compact apparatus as recited in claim 1, wherein the lubricant flow through said sample chamber is substantially vertical.

4. A compact apparatus as recited in claim 2, wherein said sample chamber is concentrically attached to the lubrication system.

5. A compact apparatus as recited in claim 1, wherein said portion of said sample chamber means allowing passage of said X-rays into and out of said sample chamber means comprises an X-ray transparent material.

6. A miniature apparatus as recited in claim 5, wherein said x-ray transparent material is selected from the group consisting of beryllium, coated beryllium, polyimides, boron, and aluminum-coated polymers.

7. A miniature apparatus as recited in claim 1, wherein said sample chamber means comprises material selected from the group consisting of light metals, nylon, bakelite, or other plastic materials.

8. A compact apparatus as recited in claim 1, wherein said source means comprises an electron-beam excited X-ray tube and a collimating/focusing assembly.

9. A compact apparatus as recited in claim 1, wherein said source means comprises an X-ray laser source capable of providing high intensity X-rays to said sample chamber means.

10. A compact apparatus as recited in claim 1, wherein said detector means comprises:
   (a) an X-ray detector configured to detect said X-rays emitted by the lubricant flowing through said sample chamber means; and
   (b) a collimating/focusing assembly configured to deliver collimated/focused X-rays emitted by the lubricant to said X-ray detector.

11. A compact apparatus as recited in claim 2, wherein said source means and said detector means are positioned on opposite sides of an x-axis formed through the center of said portion of said sample chamber allowing passage of X-rays into and out of said sample chamber, said x-axis being that is substantially perpendicular to said longitudinal axis of said sample chamber, said source means being positioned at an angle β from said x-axis, said detector means being positioned at an angle α from said x-axis.

12. A compact apparatus as recited in claim 11, wherein:
   (a) said source means is positioned at first distance from said longitudinal axis of said sample chamber; and
   (b) said detector means is positioned at a second distance from said longitudinal axis of said sample chamber.

13. A compact apparatus as recited in claim 12, wherein said first distance and said second distance are equal.

14. A compact apparatus as recited in claim 12, wherein said first distance and said second distance are not equal.

15. An apparatus for measurement of wear metal particles in a lubricant of a lubrication system of a machine, said apparatus comprising:
   (a) a tubular sample chamber having an in-line connection with the lubrication system so that said sample chamber provides a passageway through which the lubrication flows, said sample chamber having an X-ray transparent window formed therein allowing passage of X-rays so that the presence of wear metal particles can be detected in the lubricant, said sample chamber having a longitudinal axis substantially parallel to the flow of the lubricant therethrough;
   (b) a high intensity X-ray source assembly, said assembly directing said X-rays toward said sample chamber so that said X-rays pass through said window in said sample chamber and contact the lubricant, and metal particles that the lubricant may contain, flowing therethrough;
   (c) an X-ray detector, said X-ray detector configured to detect said X-rays emitted by the lubricant, and by metal particles that may be contained therein, as the lubricant and metal particles flow through said sample chamber means, said detector means generating a signal representing a quantitative measure of said X-rays emitted by the lubricant and said X-rays emitted by the metal particles, and said X-ray detector having an X-ray transparent window formed therein and having a collimating/focusing assembly configured to deliver collimated/focused X-rays to said X-ray transparent window of said X-ray detector; and
   (d) a signal processor, said signal processor being adapted to process said signal in order to determine the presence and amount of wear metal particles in the lubricant, thereby providing real-time identification and measurement of wear metal particles in the lubricant.

16. An apparatus as recited in claim 15, wherein said X-ray transparent window comprises material selected from the group consisting of beryllium, coated beryllium, polyimides, boron, and aluminum-coated polymers.

17. A apparatus as recited in claim 16, wherein said X-ray transparent material is beryllium.

18. An apparatus as recited in claim 15, wherein said sample chamber is substantially composed of a material selected from the group consisting of nylon, bakelite, or other plastic materials.

19. A apparatus as recited in claim 15, wherein said X-ray source assembly comprises:
   (a) an X-ray tube configured to emit said X-rays; and
   (b) a collimating/focusing assembly configured to focus said X-rays emitted from said X-ray tube as a high intensity, relatively small spot on said sample chamber.

20. A apparatus as recited in claim 19, wherein said X-ray collimating/focusing assembly comprises a plurality of hollow capillary tubes.

21. A apparatus as recited in claim 20, wherein said capillary tubes are substantially composed of glass.

22. A apparatus as recited in claim 20, wherein said capillary tubes have a diameter in the range of about 5 microns to about 50 microns.

23. A apparatus as recited in claim 19, wherein said X-ray collimating/focusing assembly comprises a block having a plurality of holes formed therein, said block being substantially composed of a low-density, light metal.

24. A apparatus as recited in claim 23, wherein said block is substantially composed of aluminum.

25. A apparatus as recited in claim 15, wherein said source assembly comprises an X-ray laser source capable of providing high intensity X-ray beams to said window in said sample chamber.

26. An apparatus as recited in claim 15, wherein said X-ray detector comprises a low-noise detector.

27. A apparatus as recited in claim 26, wherein said low-noise X-ray detector comprises a lithium drifted silicon detector.

28. An apparatus as recited in claim 15, further comprising a calibration device, the calibration device comprising a calibration sample configured to be movably disposed over said window in said sample chamber.

29. A apparatus as recited in claim 28, wherein said calibration sample comprises a copper disk.

30. An apparatus as recited in claim 15, wherein said source assembly and said detector are positioned on opposite sides of an x-axis formed through the center of said X-ray transparent window of said sample chamber, said x-axis being substantially perpendicular to said longitudinal axis of said sample chamber, said source assembly being positioned at an angle β from said x-axis, said detector being positioned at an angle α from said x-axis.

31. A apparatus as recited in claim 30, wherein said angle β and said angle α are not equal.

32. A apparatus as recited in claim 30, wherein said angle β and said angle α are equal.

33. A apparatus as recited in claim 15, wherein:
(a) said source assembly is laterally positioned at a first distance from said longitudinal axis of said sample chamber on the same side as said X-ray transparent window in said sample chamber; and
(b) said detector is laterally positioned at a second distance from said longitudinal axis of said sample chamber on the same side as said X-ray transparent window in said sample chamber.

34. A compact apparatus as recited in claim 33, wherein said first distance and said second distance are equal.

35. A apparatus as recited in claim 33, wherein said first distance and said second distance are not equal.

36. A miniaturized apparatus for measurement of wear metal particles in a lubricant of a lubrication system of a machine, said apparatus comprising:
(a) a non-metallic, cylindrical sample chamber having an in-line connection with the lubrication system of the machine so that said sample chamber provides a passageway through which the lubrication flows, said sample chamber having an X-ray transparent beryllium window formed therein allowing passage of X-rays so that the presence of wear metal particles can be detected in the lubricant, said sample chamber having a longitudinal axis substantially parallel to and concentric with the flow of the lubricant therethrough;
(b) a high intensity incident X-ray source assembly configured to provide a source of X-rays directed toward said sample chamber so that said X-rays pass through said window in said sample chamber and contact the lubricant, and metal particles that the lubricant may contain, flowing therethrough, said X-ray source assembly comprises:
  (i) a monochromatic, single anode X-ray tube configured to emit X-rays, said X-ray tube having an X-ray transparent window formed therein;
  (ii) a collimating/focusing assembly configured to collimate/focus said X-ray emitted from said X-ray tube as a high intensity, relatively small spot on said beryllium window in said sample chamber.
(c) an X-ray detector configured to detect said X-rays emitted by the lubricant, and by metal particles that may be contained therein, as the lubricant and metal particles flow through said sample chamber, said X-ray detector assembly generating a signal representing a quantitative measure of said X-rays emitted by the lubricant and said X-rays emitted by the metal particles, said X-ray detector assembly comprising:
  (i) a low-noise lithium drifted silicon X-ray detector configured to detect said X-rays emitted by the lubricant, and by metal particles that may be contained therein, flowing through said sample chamber, said X-ray detector having an X-ray transparent window formed therein;
  (ii) a collimating/focusing assembly capable of wide angle collection of the X-rays emitted by the lubricant, and by metal particles that may be contained therein, flowing through said sample chamber and to deliver collimated/focused X-rays to said window in said X-ray detector; and
(d) means for processing said signal in order to determine the presence and amount of wear metal particles in the lubricant, thereby providing real-time identification and measurement of wear metal particles in the lubricant.

37. A apparatus as recited in claim 36, wherein said X-ray tube comprises a pure-metal rhodium anode target.

38. A apparatus as recited in claim 36, wherein said beryllium window in said sample chamber is substantially circular.

39. A apparatus as recited in claim 36, wherein said sample chamber, said X-ray source assembly, and said X-ray detector assembly are miniaturized.

40. A apparatus as recited in claim 36, wherein said means for processing said signal from said X-ray detector to determine the presence and amount of wear metal particles in the lubricant comprises a computer system and associated software programs.

41. A method for using a compact apparatus for measurement of wear metal particles in a lubricant of a lubrication system of a machine, comprising the steps of:
(a) providing energy in the form of high intensity X-rays from an X-ray source assembly to a non-metallic sample chamber having an in-line connection to the lubrication system of the machine and through which the lubrication flows, said sample chamber having an X-ray transparent window formed therein allowing passage of X-rays so that said X-rays pass through said window in said sample chamber and contact the lubricant flowing therethrough to excite the lubricant at an atomic/molecular level;
(b) detecting said X-rays emitted from the lubricant flowing through said sample chamber using a low-noise X-ray detector assembly, said X-ray detector assembly generating a signal reflecting said X-rays emitted from the lubricant in the form of spontaneously emitted fluorescence X-rays;
(c) interpreting said signal received from said detector assembly to provide a real-time identification and measurement of the chemical composition of metal particles in the lubricant.

42. A method as recited in claim 41, further comprising the step of collimating/focusing said X-rays emitted by an X-ray tube using a collimating/focusing assembly thereby delivering a high-intensity, relatively small spot incident X-ray on said X-ray transparent window formed in said sample chamber prior to said detecting step.

43. A method as recited in claim 41, further comprising prior to said detecting step collimating or focusing said X-rays emitted from the lubricant using a collimating/focusing assembly in said X-ray detector assembly such that a collimated/focused high intensity X-ray reaches said X-ray detector assembly.

* * * * *